United States Patent [19]

Lee

[11] Patent Number: 5,596,008

[45] Date of Patent: Jan. 21, 1997

[54] 3,4-DIARYL SUBSTITUTED PYRIDINES FOR THE TREATMENT OF INFLAMMATION

[75] Inventor: Len F. Lee, St. Charles, Mo.

[73] Assignee: G. D. Searle & Co., Skokie, Ill.

[21] Appl. No.: 386,843

[22] Filed: Feb. 10, 1995

[51] Int. Cl.$^6$ .......................... C07D 213/34; A61K 31/44
[52] U.S. Cl. .......................... 514/347; 514/277; 514/357; 546/293; 546/294; 546/338; 546/339
[58] Field of Search .................................. 546/290, 300, 546/301, 303, 329, 339, 330, 334, 338, 293, 294; 514/345, 351, 357, 277, 347

[56] References Cited

U.S. PATENT DOCUMENTS

| | | | |
|---|---|---|---|
| 3,655,679 | 4/1972 | Shen et al. | 546/298 |
| 4,011,328 | 3/1977 | Pinhas et al. | 514/277 |
| 5,004,743 | 4/1991 | Young et al. | 514/227.8 |
| 5,169,857 | 12/1992 | Angerbauer et al. | 514/344 |

FOREIGN PATENT DOCUMENTS

| | | |
|---|---|---|
| 1238959 | 7/1971 | United Kingdom . |
| 96/10012 | 4/1996 | WIPO . |

Primary Examiner—C. Warren Ivy
Assistant Examiner—Lyman H. Smith
Attorney, Agent, or Firm—Joseph W. Bulock

[57] ABSTRACT

A class of substitute pyridyl compounds is described for use in treating inflammation and inflammation-related disorders. Compounds of particular interest are defined by Formula I

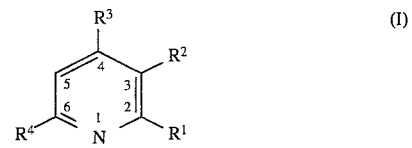

wherein $R^1$ is haloalkyl; wherein $R^2$ is aryl optionally substituted at a substitutable position with one or more radicals independently selected from alkylsulfinyl, alkyl, cyano, carboxyl, alkoxycarbonyl, haloalkyl, hydroxyl, hydroxyalkyl, haloalkoxy, amino, alkylamino, arylamino, nitro, halo, alkoxy and alkylthio; wherein $R^3$ is aryl substituted at a substitutable position with a radical selected from alkylsulfonyl and sulfamyl; and wherein $R^4$ is selected from halo, alkoxy and alkynyloxy; or a pharmaceutically-acceptable salt thereof.

21 Claims, No Drawings

3,4-DIARYL SUBSTITUTED PYRIDINES FOR THE TREATMENT OF INFLAMMATION

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel pyridines disclosed herein are such safe and also effective antiinflammatory agents furthering such efforts. The invention's compounds are found to show usefulness in vivo as antiinflammatory agents with minimal side effects. The substituted pyridinyl compounds disclosed herein preferably selectively inhibit cyclooxygenase-2 over cyclooxygenase-1.

Pyridines have been described for various uses, including the treatment of inflammation.

U.S. Pat. No. 3,655,679, to Shen et al, describes monoaryl substituted pyridine carboxylic acids as having antiinflammatory activity.

British Patent No. 1,238,959 describes 3-aryl substituted pyridyl derivatives as having antiinflammatory activity.

U.S. Pat. No. 4,011,328, to Pinhas et al, describes derivatives of 2,3-diaryl-pyridine-3-acetic acid as having antiinflammatory properties.

U.S. Pat. No. 5,004,743, to Young et al, describes monoaryl substituted pyridyl compounds as having anti-inflammatory properties.

U.S. Pat. No. 5,169,857, to Angerbauer et al, describes pyridines as useful in the treatment of hyperproteinaemia or arteriosclerosis. Specifically, 2,6-dimethyl-4-(4-fluorophenyl)-5-phenyl-pyridines are described.

The invention's pyridyl compounds are found to show usefulness in vivo as antiinflammatory agents with minimal side effects.

DESCRIPTION OF THE INVENTION

A class of substituted pyridyl compounds useful in treating inflammation-related disorders is defined by Formula I:

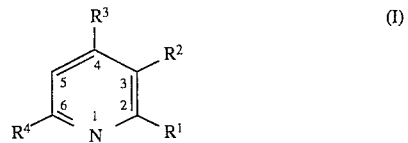

wherein $R^1$ is haloalkyl;

wherein $R^2$ is aryl optionally substituted at a substitutable position with one or more radicals independently selected from alkylsulfinyl, alkyl, cyano, carboxyl, alkoxycarbonyl, haloalkyl, hydroxyl, hydroxyalkyl, haloalkoxy, amino, alkylamino, arylamino, nitro, halo, alkoxy and alkylthio;

wherein $R^3$ is aryl substituted at a substitutable position with a radical selected from alkylsulfonyl and sulfamyl; and wherein $R^4$ is selected from halo, alkoxy and alkynyloxy;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects. Besides being useful for human treatment, these compounds are also useful for treatment of mammals, including horses, dogs, cats, rats, mice, sheep, pigs, etc.

The present compounds may also be used in co-therapies, partially or completely, in place of other conventional anti-inflammatories, such as together with steroids, NSAIDs, 5-lipoxygenase inhibitors, $LTB_4$ inhibitors and $LTA_4$ hydrolase inhibitors.

The present invention preferably includes compounds which selectively inhibit cyclooxygenase-2 over cyclooxygenase-1 and do not significantly inhibit one or more other arachidonic pathway steps, such as thromboxane $B_2$ ($TXB_2$) production.

Preferably, the compounds have a cyclooxygenase-2 $IC_{50}$ of less than about 0.1 μM, and also k5 have a selectivity ratio of cyclooxygenase-2 inhibition over cyclooxygenase-1 inhibition of at least 50, and more preferably of at least 100.

Even more preferably, the compounds have a cyclooxygenase-1 $IC_{50}$ of greater than about 0.5 μM, and more preferably of greater than 5 μM. Such preferred selectivity may indicate an ability to reduce the incidence of common NSAID-induced side effects.

A preferred class of compounds consists of those compounds of Formula I wherein $R^1$ is lower haloalkyl; wherein $R^2$ is aryl selected from phenyl, naphthyl and biphenyl, wherein $R^2$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, arylamino, nitro, halo, lower alkoxy and lower alkylthio; wherein $R^3$ is phenyl substituted at a substitutable position with a radical selected from lower alkylsulfonyl and sulfamyl; and wherein $R^4$ is selected from halo, lower alkoxy and lower alkynyloxy; or a pharmaceutically-acceptable salt thereof.

A more preferred class of compounds consists of those compounds of Formula I wherein $R^1$ is lower haloalkyl; wherein $R^2$ is phenyl optionally substituted at a substitutable position with one or more radicals independently selected from lower alkyl, lower haloalkyl, hydroxyl, lower hydroxyalkyl, lower haloalkoxy, amino, lower alkylamino, halo, lower alkoxy and lower alkylthio; wherein $R^3$ is phenyl substituted at a substitutable position with a radical selected from lower alkylsulfonyl and sulfamyl; and wherein $R^4$ is selected from halo, lower alkoxy and lower alkynyloxy; or a pharmaceutically-acceptable salt thereof.

A class of compounds of particular interest consists of those compounds of Formula I wherein $R^1$ is selected from fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl and dichloropropyl; wherein $R^2$ is phenyl optionally substituted at a substitutable position with one or more radicals independently selected from methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, fluoro, chloro, bromo, methoxy, methylenedioxy, ethoxy, propoxy, n-butoxy, ethylthio, butylthio, hexylthio and methylthio; wherein $R^3$ is phenyl substituted at a substitutable position with a radical selected from methylsulfonyl and sulfamyl; and wherein $R^4$ is selected from fluoro, chloro, bromo, methoxy, ethoxy, propoxy, n-butoxy, 2-propynyloxy and 3-butynyloxy; or a pharmaceutically-acceptable salt thereof.

A family of specific compounds of particular interest within Formula I consists of compounds and pharmaceutically-acceptable salts thereof as follows:

5-(4-fluorophenyl)-4-[(4-methylsulfonyl)phenyl]-2-propoxy-6-trifluoromethylpyridine;
2-butoxy-5-(4-fluorophenyl)-4-[(4-methylsulfonyl)phenyl]-6-trifluoromethylpyridine;
2-(3-butynyloxy)-5-(4-fluorophenyl)-4-[(4-methylsulfonyl)phenyl]-6-trifluoromethylpyridine;
2-fluoro-5-(4-fluorophenyl)-4-[(4-methylsulfonyl)phenyl]-6-trifluoromethylpyridine;
5-(4-fluorophenyl)-2-methoxy-4-[(4-methylsulfonyl)phenyl]-6-trifluoromethylpyridine;
2-ethoxy-5-(4-fluorophenyl)-4-[(4-methylsulfonyl)phenyl]-6-trifluoromethylpyridine;
2-bromo-5-(4-fluorophenyl)-4-[(4-methylsulfonyl)phenyl]-6-trifluoromethylpyridine;
5-(4-fluorophenyl)-4-[(4-methylsulfonyl)phenyl]-2-propynyloxy-6-trifluoromethylpyridine;
4-[5-(4-fluorophenyl)-2-propoxy-6-trifluoromethylpyridin-4-yl]benzenesulfonamide;
4-[2-butoxy-5-(4-fluorophenyl)-6-trifluoromethylpyridin-4-yl]benzenesulfonamide;
4-[2-(3-butynyloxy)-5-(4-fluorophenyl)-6-trifluoromethylpyridin-4-yl]benzenesulfonamide;
4-[2-fluoro-5-(4-fluorophenyl)-6-trifluoromethylpyridin-4-yl]benzenesulfonamide;
4-[5-(4-fluorophenyl)-2-methoxy-6-trifluoromethylpyridine-4-yl]benzenesulfonamide;
4-[2-ethoxy-5-(4-fluorophenyl)-6-trifluoromethylpyridin-4-yl]benzenesulfonamide;
4-[2-bromo-5-(4-fluorophenyl)-6-trifluoromethylpyridin-4-yl]benzenesulfonamide;
4-[5-(4-fluorophenyl)-2-(2-propynyloxy)-6-trifluoromethylpyridin-4-yl]benzenesulfonamide;
2-methoxy-5-(4-methylphenyl)-4-[4-(methylsulfonyl)phenyl]-6-trifluoromethyl-pyridine;
5-(4-ethylphenyl)-2-methoxy-4-[(4-(methylsulfonyl)phenyl]-6-trifluoromethyl-pyridine;
2-methoxy-4-[4-(methylsulfonyl)phenyl]-6-trifluoromethyl-5-(4-trifluoromethylphenyl)-pyridine;
5-(4-hydroxyphenyl)-2-methoxy-4-[4-(methylsulfonyl)phenyl]-6-trifluoromethyl-pyridine;
5-(4-hydroxymethylphenyl)-2-methoxy-4-[4-(methylsulfonyl)phenyl]-6-trifluoromethyl-pyridine;
2-methoxy-4-[4-(methylsulfonyl)phenyl]-6-trifluoromethyl-5-(4-trifluoromethoxyphenyl)-pyridine;
5-(4-aminophenyl)-2-methoxy-4-[4-(methylsulfonyl)phenyl]-6-trifluoromethyl-pyridine;
5-(4-chlorophenyl)-2-methoxy-4-[4-(methylsulfonyl)phenyl]-6-trifluoromethyl-pyridine;
5-(4-bromophenyl)-2-methoxy-4-[4-(methylsulfonyl)phenyl]-6-trifluoromethyl-pyridine;
2-methoxy-5-(4-methoxyphenyl)-4-[4-(methylsulfonyl)phenyl]-6-trifluoromethyl-pyridine;
2-methoxy-4-[4-(methylsulfonyl)phenyl]-5-(4-methylthiophenyl)-6-trifluoromethyl-pyridine;
2-methoxy-5-(4-methylsulfinylphenyl)-4-[4-(methylsulfonyl)phenyl]-6-trifluoromethyl-pyridine;
5-(4-cyanophenyl)-2-methoxy-4-[4-(methylsulfonyl)phenyl]-6-trifluoromethyl-pyridine;
2-methoxy-5-(4-N-methylaminophenyl)-4-[4-(methylsulfonyl)phenyl]-6-trifluoromethyl-pyridine;
4-[2-methoxy-5-(4-methylphenyl)-6-trifluoromethyl-pyridin-4-yl]benzenesulfonamide;
4-[5-(4-ethylphenyl)-2-methoxy-6-trifluoromethyl-pyridin-4-yl]benzenesulfonamide;
4-[2-methoxy-6-trifluoromethyl-5-4-trifluoromethylphenyl)-pyridin-4-yl]benzenesulfonamide;
4-[5-(4-hydroxyphenyl)-2-methoxy-6-trifluoromethyl-pyridin-4-yl]benzenesulfonamide;
4-[5-(4-hydroxymethylphenyl)-2-methoxy-6-trifluoromethyl-pyridin-4-yl]benzenesulfonamide;
4-[2-methoxy-5-(4-trifluoromethoxyphenyl)-6-trifluoromethyl-pyridin-4-yl]benzenesulfonamide;
4-[5-(4-aminophenyl)-2-methoxy-6-trifluoromethyl-pyridin-4-yl]benzenesulfonamide;
4-[5-(4-chlorophenyl)-2-methoxy-6-trifluoromethyl-pyridin-4-yl]benzenesulfonamide;
4-[5-(4-bromophenyl)-2-methoxy-6-trifluoromethyl-pyridin-4-yl]benzenesulfonamide;
4-[2-methoxy-5-(4-methoxyphenyl)-6-trifluoromethyl-pyridin-4-yl]benzenesulfonamide;

4-[2-methoxy-5-(4-methylthiophenyl)-6-trifluoromethyl-pyridin-4-yl]benzenesulfonamide;

4-[2-methoxy-5-(4-methylsulfinylphenyl)-6-trifluoromethyl-pyridin-4-yl]benzenesulfonamide;

4-[5-(4-cyanophenyl)-2-methoxy-6-trifluoromethyl-pyridin-4-yl]benzenesulfonamide; and 4-[2-methoxy -5-(4-N-methylaminophenyl)-6-trifluoromethyl-pyridin-4-yl]benzenesulfonamide.

Within Formula 2 there is a subclass of compounds of high interest represented by Formula II:

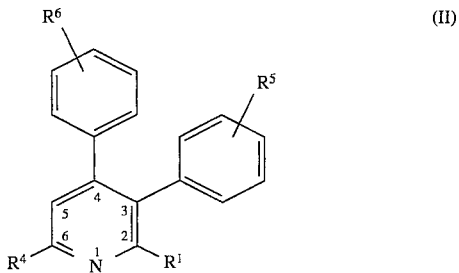

wherein $R^1$ is haloalkyl; wherein $R^4$ is selected from halo, alkoxy and alkynyloxy; wherein $R^5$ is halo; and wherein $R^6$ is alkylsulfonyl; or a pharmaceutically-acceptable salt thereof.

A preferred class of compounds consists of those compounds of Formula II wherein $R^1$ is lower haloalkyl; wherein $R^4$ is selected from halo, lower alkoxy and lower alkynyloxy; wherein $R^5$ is halo; and wherein $R^6$ is lower alkylsulfonyl; or a pharmaceutically-acceptable salt thereof.

A class of compounds of particular interest consists of those compounds of Formula II wherein $R^1$ is trifluoromethyl; wherein $R^4$ is selected from fluoro, chloro, bromo, iodo, methoxy, ethoxy, isopropoxy, tert-butoxy, propoxy, butoxy, isobutoxy, pentoxy, 2-propynyloxy, and 3-butynyloxy; wherein $R^5$ is fluoro, chloro, bromo, iodo; and wherein $R^6$ is methylsulfonyl; or a pharmaceutically-acceptable salt thereof.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl; isopropyl, n-butyl, isobutyl, sec-butyl, tert-butyl, pentyl, iso-amyl, hexyl and the like. The term "alkynyl" embraces linear or branched radicals having at least one carbon-carbon double bond of two to about twenty carbon atoms or, preferably, one to about twelve carbon atoms. More preferred alkyl radicals are "lower alkynyl" radicals having two to about six carbon atoms. Examples of alkynyl radicals include 2-propynyl, 3-butynyl and 2-butynyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals Include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, no provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cycloalkoxy" embraces radicals having cycloalkyl radicals, as defined above, attached to an alkoxy radical. The term "alkynyloxy" embraces radicals having alkynyl portions of two to about ten carbon atoms attached to an oxygen atom. More preferred alkynyloxy radicals are "lower alkynyloxy" radicals having two to six carbon atoms. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.]tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3-to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.]etc! .; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denotes $NH_2O_2S$—. The term "acyl" denotes a radical provided by the residue after removal of hydroxyl from an organic acid. Examples of such acyl radicals include alkanoyl and aroyl radicals. The terms "carboxy" or "carboxyl", whether used alone or with other terms, such as "carboxyalkyl", denotes —CO$_2$H. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–IV, wherein the $R^1$–$R^6$ substituents are as defined for Formula I–II, above, except where further noted.

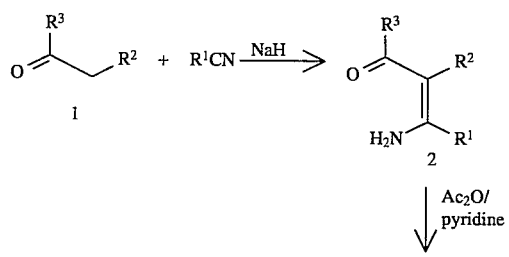

-continued
Scheme I

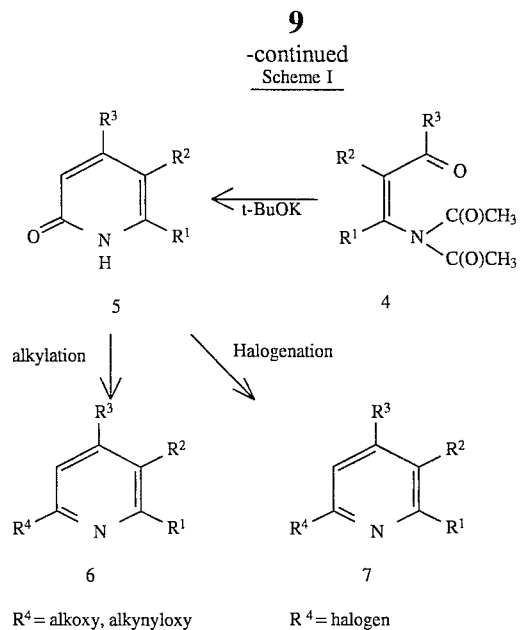

R⁴ = alkoxy, alkynyloxy    R⁴ = halogen

Scheme I shows the multi-step method to form the 3,4-substituted pyridines 6 and 7 of the current invention. The compounds of this invention can be prepared from 1,2-diarylethanones as prepared by a procedure similar to the that described in U.S. Pat. No. 3,647,858. Reaction of diarylethanone 1 with sodium hydride and an activated nitrile, such as gaseous trifluoroacetonitrile, gives a mixture of enaminoketone 2 and 4,5-diarylpyrimidine. Reaction of 2 with excess acetic anhydride and pyridine yields N,N-diacetylenaminoketone 4. Cyclization of 4 with potassium tert-butoxide in THF produces 4,5-diaryl-2-pyridone 5. Pyridone 5 can be alkylated with an alkyl or alkynyl halide (R⁴X) to give 2-alkoxypyridines 6. Halogenation of 5 5 with a phosphorus oxyhalide (POX₃) or a phosphorus pentahalide (PX₅) yields the 2-halopyridines 7.

Scheme II

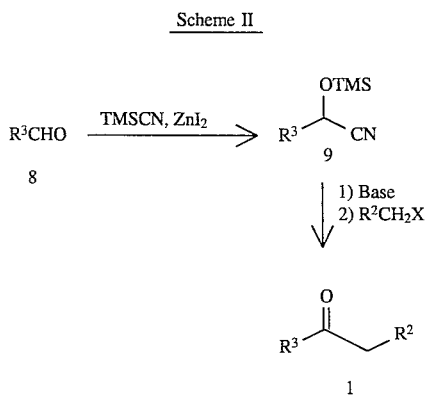

Scheme II shows a three step method of forming diarylethanone 1 for use in Synthetic Scheme I. In step 1, a silylating agent, such as trimethylsilyl cyanide, is added to a solution of substituted aldehyde 8 (R³CHO) in a solvent such as dichloromethane. After the addition is complete, zinc iodide is added to give the protected ketone 9. In step 2, the protected ketone 9 is added to a solution of base such as an alkyllithium reagent (i.e. lithium bis(trimethylsilyl)amide) in an appropriate solvent such as tetrahydrofuran. In step 3, a solution of the halo compound (where X is halo) in an appropriate solvent, such as tetrahydrofuran, ms added. Aqueous hydrochloric acid is added to yield the ketone 1.

Scheme III

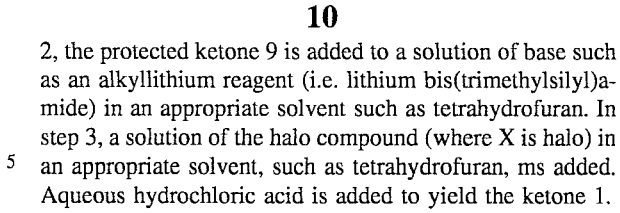

Scheme III shows a method to form the alkylsulfonylphenyl substituted pyridines 11 of the current invention by oxidation of alkylthio or alkylsulfinyl derivatives 10. Aqueous hydrogen peroxide (30%) is added to a suspension of a (methylthio)phenyl substituted pyridine 10 in acetic acid. The mixture is stirred while heating to about 100° C. to yield the sulfone 11. Alternatively, meta-chloroperoxybenzoic acid (MCPBA), and other oxidizing agents can be used to form sulfones 11.

Scheme IV

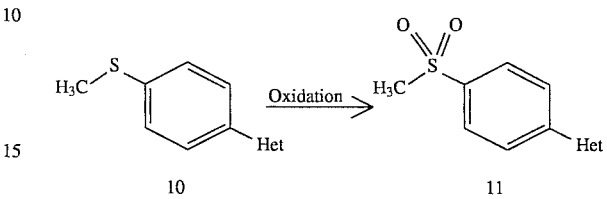

Synthetic Scheme IV shows the three step procedure used to prepare sulfonamide antiinflammatory agents 13 from their corresponding methyl sulfones 12. In step one, THF solutions of the methyl sulfones 12 at −78° C. are treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxylamine-O-sulfonic acid is added to provide the corresponding sulfonamide antiinflammatory agents 13 of this invention.

The following examples contain detailed descriptions of the methods of preparation of compounds of Formula I-II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLES 1

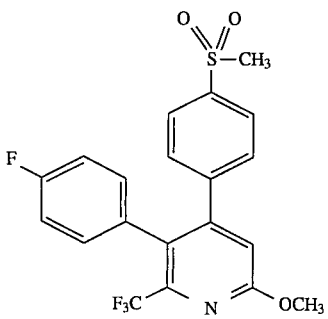

5-(4-Fluorophenyl)-2-methoxy-4-[4-(methylsulfonyl)phenyl]-6-(trifluoromethyl)pyridine Step 1: Preparation of 2-(4-fluorophenyl)-1-[4-(methylthio)phenyl]ethanone As described in U.S. Pat. No. 3,647,858, a mixture of 4-methylthiophenylacetic acid (13.8 g, 0.076 ml) and 30 ml of thionyl chloride was held at reflux for 1.5 hours and concentrated. To this residue was added an additional 30 ml of thionyl chloride and the mixture was held at reflux for 3 hours and reconcentrated. The residue was dissolved in carbon disulfide (150 ml) and treated with fluorobenzene (14.8 g, 0.15 ml), followed by aluminum chloride (21.8 g, 0.17 ml) and stirred for 18 hours. The mixture was concentrated in vacuo. The residue was treated with ice water causing HCl evolution and formation of a solid. The solid was dissolved in methylene chloride, dried and concentrated. The residue was washed with ether and with sat. NaHCO₃, and filtered. The insoluble solid was dissolved in chloroform and dried over MgSO₄, filtered and concentrated in vacuo. The residue was recrystallized from chloroform/hexane to yield 2.91 g of tan solid.

Step 2: Preparation of 3-amino-2-(4-fluorophenyl)-1-[4-(methylthio)phenyl]-4,4,4,-trifluoro-2-butenone To a mixture of 1.56 g (0.052 mole) of 80% sodium hydride oil dispersion, and 20 mL of anhydrous dimethylformamide (DMF) was added a solution of 13 g (0.05 mole) of 2-(4-fluorophenyl)-1-[4-(methylthio)phenyl]ethanone from Step 1 in 80 mL of anhydrous in 20 minutes. The resulting yellow solution was cooled to 0°–5° C. To this solution was passed 11 g (0.12 mole) of gaseous trifluoroacetonitrile in 20 minutes. The reaction mixture was poured into water and extracted with methylene chloride. The methylene chloride extract was washed with brine, dried over MgSO₄ and concentrated in vacuo to give a semi-solid. This semisolid was heated with 10% ethyl acetate-hexane and filtered to recover 4.0 g (31%) of the starting ketone. The filtrate was concentrated and the residue was crystallized from 10% ethyl acetate-hexane to give 3.78 g (21%) of the desired product. A portion of this material was further purified by HPLC (10% ethyl acetate-hexane) to give 2.0 g of pure material, mp 122.5°–124.5 ° C. The mother liquor was concentrated and the residue was further purified by HPLC. The first fraction was 3.28 g (15%) of 2,4-bis(trifluoromethyl)-6-(4-fluorophenyl)-5-[4-(methylthio)phenyl] pyrimidine. The second fraction was additional 3.25 g (19%) of the desired product.

Step 3: Preparation of 3-(N,N-diacetylamino)-2-(4-fluorophenyl)-1-[4-(methylthio)phenyl]-4,4,4,-trifluoro-2-butenone A mixture of 4.73 g of the ketone of Step 2, 29 g of acetic anhydride and 2.3 g (0.029 mole) of pyridine was held at reflux for 8 hours and concentrated in vacuo to remove excess acetic anhydride and pyridine to give the crude protected amino ketone which was used in the next step.

Step 4: Preparation of 5-(4-fluorophenyl)-4-[4-(methylthio)phenyl]-6-(trifluoromethyl)-2-oxy-pyridine To a solution of the amino ketone of Step 3 in 20 mL of dry THF was added 3.8 g (0.034 mole) of potassium tert-butoxide causing an exotherm. The reaction mixture was held at reflux for 30 minutes and was let stand overnight. The reaction mixture was poured into 50 mL of 3N HCl and extracted with ether. The ether extract was washed with brine, dried over MgSO₄, and concentrated in vacuo. The residual solid was heated with methylene chloride, cooled and filtered to give 2.53 g (53%) of a light yellow solid: mp 221°–224° C.

Step 5: Preparation of 5-(4-fluorophenyl)-4-[4-(methylsulfonyl)phenyl]-6-(trifluoromethyl)-2-oxo-pyridine To a solution of 2.05 g (1.37 mMol) of the oxy-pyridine of Step 4 in 20 mL of glacial acetic acid was added 2.4 g (21 mMol) of 30% hydrogen peroxide. The reaction mixture was heated at 60° C. for 1 hour and at 80° C. for 6 hours. The mixture was poured into water solution containing 6 g of sodium sulfite. The insoluble tan solid was filtered and air dried to give 2.05 g of solid: mp 232°–242° C.

Step 6: Preparation of 5-(4-fluorophenyl)-2-methoxy-4-[4-(methylsulfonyl)phenyl]-6-(trifluoromethyl)pyridine A mixture of 0.16 g (0.39 mMol) of the sulfone of Step 5, 0.2 g of potassium carbonate and 4.0 g of iodomethane, and 5 mL of DMF was stirred for 3 hours, poured into water and extracted with ether. The ether extract was washed with brine, dried over MgSO₄ and filtered through silica gel. The filtrate was concentrated in vacuo and the residue was crystallized from hexane to give 5-(4-fluorophenyl)-2-methoxy-4-[4-(methylsulfonyl)phenyl]-6-(trifluoromethyl)pyridine as a white solid (0.17 g): mp 166.5°–168 ° C.

EXAMPLE 2

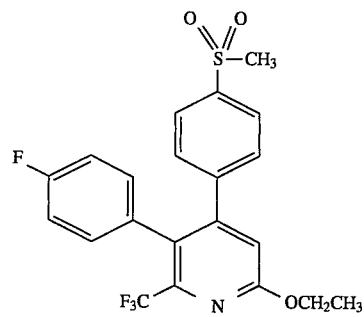

2-Ethoxy-5-(4-fluorophenyl)-4-[4-(methylsulfonyl)phenyl]-6-(trifluoromethyl)pyridine A mixture of 0.11 g of 5-(4-fluorophenyl)-4-[4(methylsulfonyl)phenyl]-6-(trifluoromethyl)-2-oxo-pyridine (step 5 of Example 1), 3,3 g of bromoethane, 0.2 g of potassium carbonate, and 5 mL of dimethyl formamide (DMF) was stirred for 20 hours and concentrated in vacuo. The residue was triturated with water and extracted with methylene chloride. The methylene chloride extract was dried over MgSO₄ and filtered through silica gel. The filtrate was reconcentrated in vacuo and the residue was crystallized from methylene chloride/hexane to give 31 mg of solid: mp 168.5°–170.5° C.

13
EXAMPLE 3

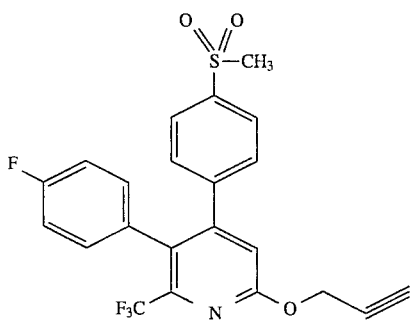

5-(4-Fluorophenyl)-4-[4-(methylsulfonyl)phenyl]-2-
(2-propynyloxy)-6-(trifluoromethyl)pyridine A mixture of 0.11 g of 5-(4-fluorophenyl)-4-[4-(methylsulfonyl)phenyl]-6-(trifluoromethyl)-2-oxo-pyridine (step 5 of Example 1), 2.5 g of propargyl bromide, 0.3 g of potassium carbonate, and 5 mL of DMF was stirred for 60 hours and concentrated in vacuo. The residue was triturated with water and extracted with methylene chloride. The methylene chloride extract was dried over $MgSO_4$ and filtered through silica gel. The filtrate was reconcentrated in vacuo and the residue was crystallized from ether/hexane to give 56 mg of white solid: mp 138°–139° C.

EXAMPLE 4

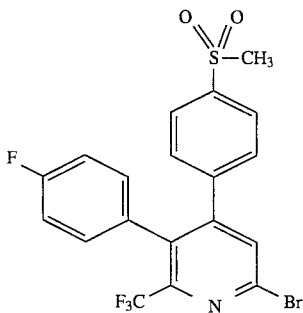

2-Bromo-5-(4-fluorophenyl)-4-[4-(methylsulfonyl)
phenyl]-6-(trifluoromethyl)pyridine A mixture of 0.35 g of 5-(4-fluorophenyl)-4-[4-(methylsulfonyl)phenyl]-6-(trifluoromethyl)-2-oxo-pyridine (step 5 of Example 1), 3 g of phosphorus pentabromide, 0.3 g of potassium bromide and 10 mL of 1,2-dichlorobenzene was held at reflux for 2 hours. The reaction mixture was cooled. An addition 3.7 g of phosphorus pentabromide was added to the reaction mixture and the reaction mixture was held at 90° C. for 8 hours, and at 180°–190° C. for 2 days. The reaction mixture was cooled and stirred with water and methylene chloride. The methylene chloride layer was dried over $MgSO_4$ and filtered through silica gel. The methylene chloride filtrate was concentrated in vacuo and the residue was purified by HPLC (20% ethyl acetate/hexane then 50% ethyl acetate/hexane). The fraction eluted with 50% ethyl acetate/hexane yielded a solid. Recrystallization from methylene chloride/hexane yielded 150 mg of white solid: mp 187.5°–189° C.

14
BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-steroidal Anti-Inflammatory Drugs* (J. Lombardino, ed. 1985)). The % inhibition shows the % decrease from control paw volume determined in this procedure and the data for selected compounds in this invention are summarized in Table I.

TABLE I

| RAT PAW EDEMA | |
| --- | --- |
| | % Inhibition @ 20 mg/kg body weight |
| Example 1 | 12 |

Evaluation of COX-1 and COX-2 activity in vitro

The compounds of this invention exhibited inhibition in vitro of COX-2. The COX-2 inhibition activity of the compounds of this invention illustrated in the Examples was determined by the following methods.

a. Preparation of recombinant COX baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells ($2\times10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^7$–$10^8$ pfu/ml) stocks of virus were prepared. For large scale production, SF9 insect cells were infected in 10 liter fermentors ($0.5\times10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propane-sulfonate (CHAPS). The homogenate was centrifuged at 10,000×G for 30 minutes, and the resultant supernatant was stored at −80° C. before being assayed for COX activity.

b. Assay for COX-1 and COX-2 activity:

COX activity was assayed as PGE2 formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE II

| Example | COX-1 murine $ID_{50}$ μM | COX-2 murine $ID_{50}$ μM |
|---|---|---|
| 1 | .3 | >30 |
| 2 | .3 | >30 |
| 3 | .2 | >30 |
| 4 | .6 | >100 |

Also embraced within this invention is a class lid of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administeredper os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

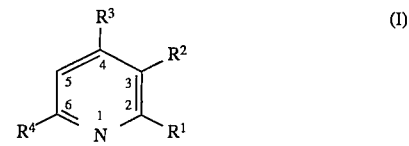

wherein $R^1$ is haloalkyl;

wherein $R^2$ is aryl optionally substituted at a substitutable position with one or more radicals independently selected from alkylsulfinyl, alkyl, cyano, carboxyl, alkoxycarbonyl, haloalkyl, hydroxyl, hydroxyalkyl, haloalkoxy, amino, alkylamino, arylamino, nitro, halo, alkoxy and alkylthio;

wherein $R^3$ is aryl substituted at a substitutable position with a radical selected from alkylsulfonyl and sulfamyl; and wherein $R^4$ is selected from halo, alkoxy and alkynyloxy;

or a pharmaceutically-acceptable salt thereof.

2. Compound of claim 1 wherein $R^1$ is lower haloalkyl; wherein $R^2$ is aryl selected from phenyl, naphthyl and biphenyl, wherein $R^2$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, arylamino, nitro, halo, lower alkoxy and lower alkylthio; wherein $R^3$ is phenyl substituted at a substitutable position with a radical selected from lower alkylsulfonyl and sulfamyl; and wherein $R^4$ is selected from halo, lower alkoxy and lower alkynyloxy; or a pharmaceutically-acceptable salt thereof.

3. Compound of claim 2 wherein $R^1$ is lower haloalkyl; wherein $R^2$ is phenyl optionally substituted at a substitutable position with one or more radicals independently selected from lower alkyl, lower haloalkyl, hydroxyl, lower hydroxyalkyl, lower haloalkoxy, amino, lower alkylamino, halo, lower alkoxy and lower alkylthio; wherein $R^3$ is phenyl substituted at a substitutable position with a radical selected from lower alkylsulfonyl and sulfamyl; and wherein $R^4$ is selected from halo, lower alkoxy and lower alkynyloxy; or a pharmaceutically-acceptable salt thereof.

4. Compound of claim 3 wherein R¹ is selected from fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl and dichloropropyl; wherein R² is phenyl optionally substituted at a substitutable position with one or more radicals independently selected from methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, fluoro, chloro, bromo, methoxy, methylenedioxy, ethoxy, propoxy, n-butoxy, ethylthio, butylthio, hexylthio and methylthio; wherein R³ is phenyl substituted at a substitutable position with a radical selected from methylsulfonyl and sulfamyl; and wherein R⁴ is selected from fluoro, chloro, bromo, methoxy, ethoxy, propoxy, n-butoxy, 2-propynyloxy and 3-butynyloxy; or a pharmaceutically-acceptable salt thereof.

5. Compound of claim 4 selected from compounds, and their pharmaceutically acceptable salts, of the group consisting of 5-(4-fluorophenyl)-4-[(4-methylsulfonyl)phenyl]-2-propoxy-6-trifluoromethylpyridine;

2-butoxy-5-(4-fluorophenyl)-4-[(4-methylsulfonyl)phenyl]-6-trifluoromethylpyridine;

2-(3-butynyloxy)-5-(4-fluorophenyl)-4-[(4-methylsulfonyl)phenyl]-6-trifluoromethylpyridine;

2-fluoro-5-(4-fluorophenyl)-4-[(4-methylsulfonyl)phenyl]-6-trifluoromethylpyridine;

5-(4-fluorophenyl)-2-methoxy-4-[(4-methylsulfonyl)phenyl]-6-trifluoromethylpyridine;

2-ethoxy-5-(4-fluorophenyl-4-[(4-methylsulfonyl)phenyl]-6-trifluoromethylpyridine;

2-bromo-5-(4-fluorophenyl)-4-[(4-methylsulfonyl)phenyl]-6-trifluoromethylpyridine;

5-(4-fluorophenyl)-4-[(4-methylsulfonyl)phenyl]-2-(2-propynyloxy)-6-trifluoromethylpyridine;

4-[5-(4-fluorophenyl)-2-propoxy-6-trifluoromethylpyridin-4-yl]benzenesulfonamide;

4-[2-butoxy-5-(4-fluorophenyl)-6-trifluoromethylpyridin-4-yl]benzenesulfonamide;

4-[2-(3-butynyloxy)-5-(4-fluorophenyl)-6-trifluoromethylpyridin-4-yl]benzenesulfonamide;

4-[2-fluoro-5-(4-fluorophenyl)-6-trifluoromethylpyridin-4-yl]benzenesulfonamide;

4-[5-(4-fluorophenyl)-2-methoxy-6-trifluoromethylpyridin-4-yl]benzenesulfonamide;

4-[2-ethoxy-5-(4-fluorophenyl)-6-trifluoromethylpyridin-4-yl]benzenesulfonamide;

4-[2-bromo-5-(4-fluorophenyl)-6-trifluoromethylpyridin-4-yl]benzenesulfonamide;

4-[5-(4-fluorophenyl)-2-(2-propynyloxy)-6-trifluoromethylpyridin-4-yl]benzenesulfonamide;

2-methoxy-5-(4-methylphenyl)-4-[4-(methylsulfonyl)phenyl]-6-trifluoromethyl-pyridine;

5-(4-ethylphenyl)-2-methoxy-4-[4-(methylsulfonyl)phenyl]-6-trifluoromethyl-pyridine;

2-methoxy-4-[4-(methylsulfonyl)phenyl]-6-trifluoromethyl-5-(4-trifluoromethylphenyl)pyridine;

5-(4-hydroxyphenyl)-2-methoxy-4-[4-(methylsulfonyl)phenyl]-6-trifluoromethyl-pyridine;

5-(4-hydroxymethylphenyl)-2-methoxy-4-[4-(methylsulfonyl)phenyl]-6-trifluoromethyl-pyridine;

2-methoxy-4-[4-(methylsulfonyl)phenyl]-6-trifluoromethyl-5-(4-trifluoromethoxyphenyl)pyridine;

5-(4-aminophenyl)-2-methoxy-4-[4-(methylsulfonyl)phenyl]-6-trifluoromethyl-pyridine;

5-(4-chlorophenyl)-2-methoxy-4-[4-(methylsulfonyl)phenyl]-6-trifluoromethyl-pyridine;

5-(4-bromophenyl)-2-methoxy-4-[4-(methylsulfonyl)phenyl]-6-trifluoromethyl-pyridine;

2-methoxy-5-(4-methoxyphenyl)-4-[4-(methylsulfonyl)phenyl]-6-trifluoromethyl-pyridine;

2-methoxy-4-[4-(methylsulfonyl)phenyl]-5-(4-methylthiophenyl)-6-trifluoromethyl-pyridine 2-methoxy-5-(4-methylsulfinylphenyl)-4-[4-(methylsulfonyl)phenyl]-6-trifluoromethyl-pyridine 5-(4-cyanophenyl)-2-methoxy-4-[4-(methylsulfonyl)phenyl]-6-trifluoromethyl-pyridine 2-methoxy-5-(4-N-methylaminophenyl)-4-[4-(methylsulfonyl)phenyl]-6-trifluoromethyl-pyridine 4-[2-methoxy-5-(4-methylphenyl)-6-trifluoromethylpyridin-4-yl]benzenesulfonamide;

4-[5-(4-ethylphenyl)-2-methoxy-6-trifluoromethylpyridin-4-yl]benzenesulfonamide;

4-[2-methoxy-6-trifluoromethyl-5-(4-trifluoromethylphenyl)-pyridin-4-yl]benzenesulfonamide;

4-[5-(4-hydroxyphenyl)-2-methoxy-6-trifluoromethylpyridin-4-yl]benzenesulfonamide;

4-[5-(4-hydroxymethylphenyl)-2-methoxy-6-trifluoromethyl-pyridin-4-yl]benzenesulfonamide;

4-[2-methoxy-5-(4-trifluoromethoxyphenyl)-6-trifluoromethyl-pyridin-4-yl]benzenesulfonamide;

4-[5-(4-aminophenyl)-2-methoxy-6-trifluoromethylpyridin-4-yl]benzenesulfonamide;

4-[5-(4-chlorophenyl)-2-methoxy-6-trifluoromethylpyridin-4-yl]benzenesulfonamide;

4-[5-(4-bromophenyl)-2-methoxy-6-trifluoromethylpyridin-4-yl]benzenesulfonamide;

4-[2-methoxy -5-(4-methoxyphenyl)-6-trifluoromethylpyridin-4-yl]benzenesulfonamide;

4-[2-methoxy-5-(4-methylthiophenyl)-6-trifluoromethylpyridin-4-yl]benzenesulfonamide;

4-[2-methoxy-5-(4-methylsulfinylphenyl)-6-trifluoromethyl-pyridin-4-yl]benzenesulfonamide 4-[5-(4-cyanophenyl)-2-methoxy-6-trifluoromethylpyridin-4-yl]benzenesulfonamide; and 4-[2-methoxy-5-(4-N-methylaminophenyl)-6-trifluoromethyl-pyridin-4-yl]benzenesulfonamide.

6. A compound of Formula II

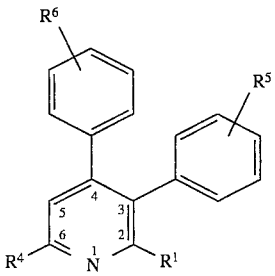

(II)

wherein R¹ is haloalkyl; wherein R⁴ is selected from halo, alkoxy and alkynyloxy; wherein R⁵ is halo; and wherein R⁶ is alkylsulfonyl; or a pharmaceutically-acceptable salt thereof.

7. A pharmaceutical composition comprising a therapeutically-effective amount of a compound, said compound selected from a family of compounds of claim 1; or a pharmaceutically-acceptable salt thereof.

8. A pharmaceutical composition comprising a therapeutically-effective amount of a compound, said compound selected from a family of compounds of claim 2; or a pharmaceutically-acceptable salt thereof.

9. A pharmaceutical composition comprising a therapeutically-effective amount of a compound, said compound selected from a family of compounds of claim 3; or a pharmaceutically-acceptable salt thereof.

10. A pharmaceutical composition comprising a therapeutically-effective amount of a compound, said compound selected from a family of compounds of claim 4; or a pharmaceutically-acceptable salt thereof.

11. A pharmaceutical composition comprising a therapeutically-effective amount of a compound, said compound selected from a family of compounds of claim 5; or a pharmaceutically-acceptable salt thereof.

12. A method of treating inflammation or an inflammation-associated disorder in a subject, said method comprising administering to the subject having or susceptible to such inflammation or inflammation-associated disorder, a therapeutically-effective amount of a compound of claim 1; or a pharmaceutically-acceptable salt thereof.

13. A method of treating inflammation or an inflammation-associated disorder in a subject, said method comprising administering to the subject having or susceptible to such inflammation or inflammation-associated disorder, a therapeutically-effective amount of a compound of claim 2; or a pharmaceutically-acceptable salt thereof.

14. A method of treating inflammation or an inflammation-associated disorder in a subject, said method comprising administering to the subject having or susceptible to such inflammation or inflammation-associated disorder, a therapeutically-effective amount of a compound of claim 3; or a pharmaceutically-acceptable salt thereof.

15. A method of treating inflammation or an inflammation-associated disorder in a subject, said method comprising administering to the subject having or susceptible to such inflammation or inflammation-associated disorder, a therapeutically-effective amount of a compound of claim 4; or a pharmaceutically-acceptable salt thereof.

16. A method of treating inflammation or an inflammation-associated disorder in a subject, said method comprising administering to the subject having such inflammation or inflammation-associated disorder, a therapeutically-effective amount of a compound of claim 5; or a pharmaceutically-acceptable salt thereof.

17. The method of claim 12 for use in treatment of inflammation.

18. The method of claim 12 for use in treatment of an inflammation-associated disorder.

19. Thee method of claim 18 wherein the inflammation-associated disorder is arthritis.

20. The method of claim 18 wherein the inflammation-associated disorder is pain.

21. The method of claim 18 wherein the inflammation-associated disorder is fever.

* * * * *